United States Patent

Grady

[11] Patent Number: 5,847,404
[45] Date of Patent: Dec. 8, 1998

[54] BREAST SHIELD

[76] Inventor: Wanda Ann Grady, 502 W. Sycamore St., Stillwater, Minn. 55082

[21] Appl. No.: 712,338

[22] Filed: Sep. 11, 1996

Related U.S. Application Data

[60] Provisional application No. 60/005,095 Sep. 11, 1995.
[51] Int. Cl.[6] ............................................. A61F 13/00
[52] U.S. Cl. ............................................. 250/515.1
[58] Field of Search .............................. 250/515.1, 516.1, 250/519.1; 128/846, 858, 890; 2/15, 92, 463

[56] References Cited

U.S. PATENT DOCUMENTS

| | | | |
|---|---|---|---|
| 3,061,491 | 10/1962 | Sherrard et al. | 250/515.1 |
| 4,339,035 | 7/1982 | Marcus et al. | 250/515.1 |
| 4,674,133 | 6/1987 | Oschner | 2/206 |
| 4,745,916 | 5/1988 | Seber | 128/155 |

*Primary Examiner*—Kiet T. Nguyen
*Attorney, Agent, or Firm*—Burd, Bartz & Gutenkauf

[57] ABSTRACT

An ultra violet radiation shield for protecting a person's skin from ultra violet radiation has a backing member associated with an adhesive for securing the backing member to a person's skin. An ultra violet radiation blocking layer for protecting a person's skin is associated with the backing member.

11 Claims, 4 Drawing Sheets

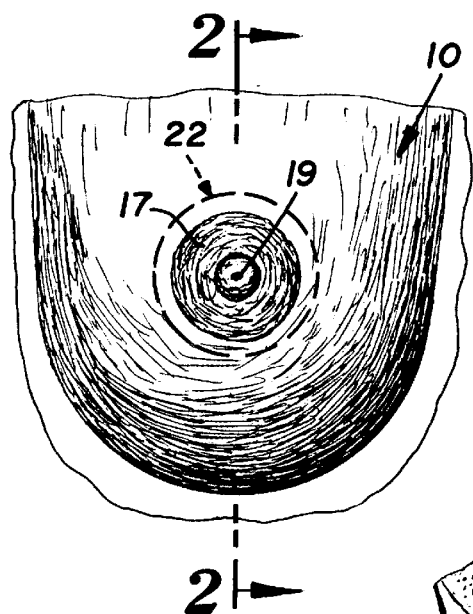
*FIG.1*
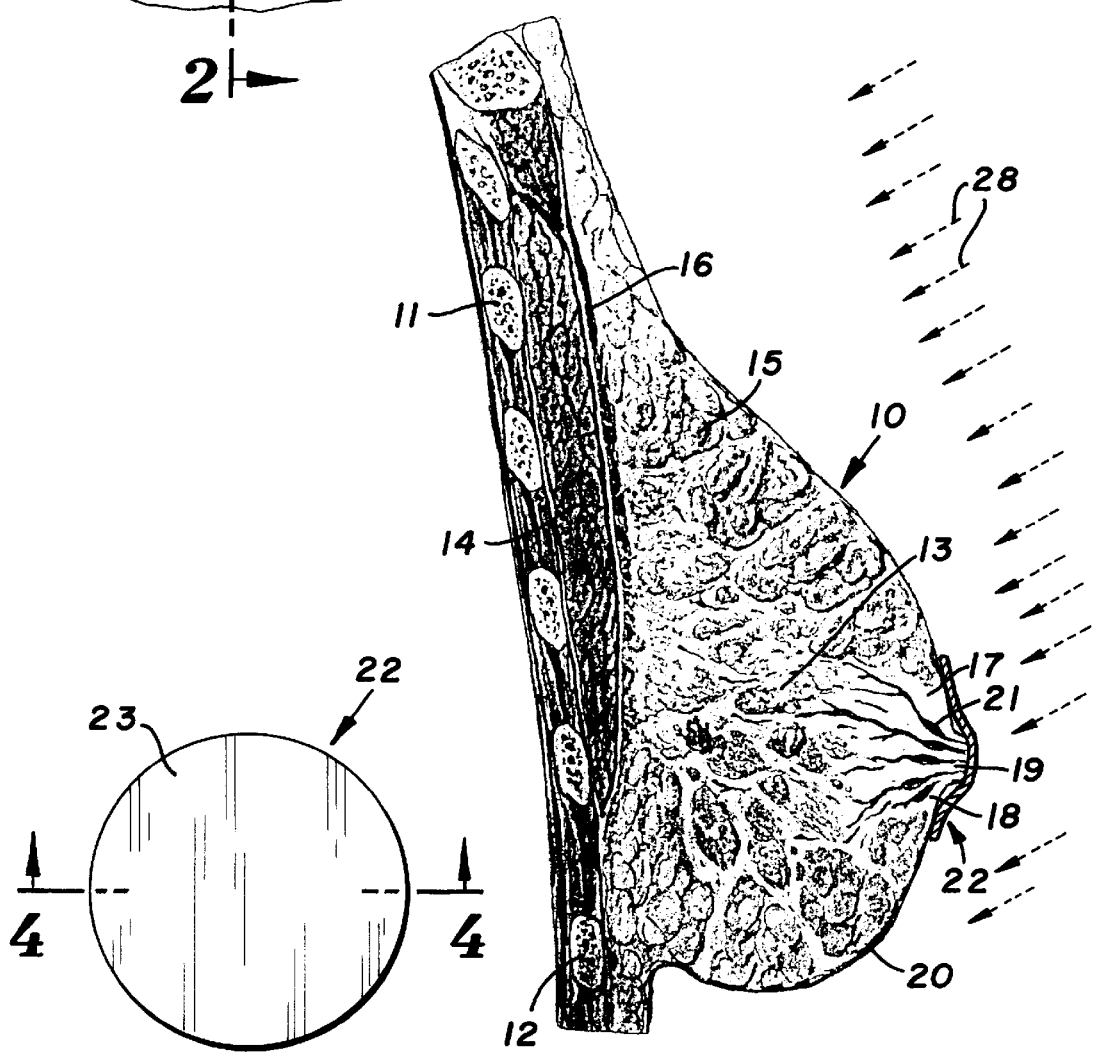
*FIG.3*
*FIG.2*

BREAST SHIELD

CROSS REFERENCE TO RELATED APPLICATION

This application is a continuation-in-part of U.S. provisional application Ser. No. 60/005,095 filed Sep. 11, 1995.

BACKGROUND OF THE INVENTION

It is known that the deleterious effects of sunlight on biological systems are due mostly entirely to radiation within the ultra violet spectrum within the sun's emission. The quantity and quality of ultra violet radiation at the earth's surface depends on the energy output of the sun and the transmission properties of the atmosphere. Ultra violet radiation in the range of 290–320 nanometers is the most significant part of the terrestrial ultra violet spectrum which are largely controlled by ozone. In artificial light sources, shorter wave lengths are also responsible for producing adverse effects on biological systems. The biological effects that result from ultra violet radiation are initiated by photo-chemical absorption by molecules of biological significance. The most important of these are the nucleic acids, proteins and other molecules. Cells and viruses can be inactivated by exposure to ultra violet radiation. They loose their ability to reproduce. The known biological effects to humans due to exposure of solar ultra violet radiation appear to be limited to the skin and to the eyes. The penetration of the ultra violet radiation into skin is about 1 millimeter and is absorbed by ocular tissues in the eye before it reaches the retina. The responses of the skin to ultra violet radiation include sun burn, tanning and vitamin D production, photo-aging and skin cancer. The cause of sunburn is the transfer of energy from ultra violet radiation to the skin, resulting in generation of excited oxygen species that can damage lipid-rich membranes with the subsequent activation of the chemical releases mediators of inflammation. Ultra violet radiation releases arachidonic acid, which is quickly oxidized to a variety of biologically active metabolites. When arachidonic acid is oxidized, prostaglandins create marked erythema and leukotrines which can cause erythema and edema. The free radicals created by ultra violet radiation can damage the DNA of the cells, resulting in permanent injury, premature aging, premalignant growths of the skin, and carcinogenesis.

A socially-desirable consequence of exposure to unfiltered sunlight is the delayed pigmentation of the skin, known as tanning. Sun beds and tanning booths have been designed to subject the human body to ultra violet radiation to produce the tanning or facultative pigmentation of the skin.

The application of dermatologically acceptable carriers, commonly labeled topical sun screens, have been shown to inhibit photo-aging of skin exposed to solar radiation. These products can take the form of lotions, creams, gels and sold compositions. Typical compositions contain water and/or alcohols and emollients, such as hydrocarbon oils and waxes; silicone oils; vegetable, animal or marine fats or oils; glyceride derivatives; fatty acids; lanolin; wax esters; sterols; and, phospholipids. These products also inhibit the tanning of the skin, as well as reduce the risk of skin cancer. Skin cancer is the most common human cancer. Chronic exposure to solar ultra violet radiation is an important cause of this cancer.

Humans using sun beds or tanning booths are exposed to intensive ultra violet radiation. Adhesive strips, shoulder pads, roll-up towels, are used to protect sensitive parts of the body, such as the breasts and other private body parts, from burning and over-exposure. Swimsuit tops are also used to protect the nipple area of the breast. This results in unwanted lines in the adjacent skin, which are objectionable in advertising art.

SUMMARY OF THE INVENTION

The invention relates to shields for protecting a person from ultra violet radiation emanating from the sun's emission or artificial ultra violet sources, such as tanning booths. The shield is a generally flat backing member having opposite sides. An adhesive is located adjacent one side of the backing member for holding the backing member adjacent a person's skin in a selected desired location. The adhesive is covered with a removable strip or liner to protect the adhesive during storage and transportation. The liner is a paper sheet that is removable from the adhesive so that the adhesive can be placed in a selected location on a person's skin to hold the backing member adjacent the skin. An ultra violet radiation blocking substance is associated with the backing member for protecting the skin from ultra violet radiation. In one form of the shield, the backing member, the adhesive and the ultra violet radiation blocking substance, are sandwiched and secured together to form the ultra violet radiation shield. The ultra violet radiation blocking substance can be an ink or resin that reflects ultra violet radiation. The blocking substance can be incorporated into either the adhesive or the backing member.

In one form of the invention, the ultra violet radiation shield is used to protect the areola and nipple from a primate's breast from ultra violet radiation. The shield is used in association with sun beds and tanning booths which exposes the person's skin to intensive ultra violet radiation. The shield protects the sensitive areola and nipple from the ultra violet radiation without producing unwanted lines in a person's adjacent skin. The shield includes a backing member having a first and second size of a size to cover the areola and nipple of a primate's breast. The backing member has a circular configuration with a diameter between 1½–2½ cm. One side of the backing member is covered with an adhesive which is used to releasably hold the backing member on the areola. A liner is located over the adhesive to protect the adhesive during storage of the shield. The liner is removable from the adhesive so that the adhesive is used to secure the backing member to the areola. An ultra violet radiation blocking substance is associated with the backing member for protecting the areola and nipple from ultra violet radiation.

The ultra violet radiation shield can be used to protect other parts of the human body from burning and over-exposure from ultra violet radiation. The size and shape of the shield may vary in accordance with the body part to be protected. The outer surface of the backing member can be colored with various shades of colors and include artistic and ornamental designs including flowers, candy, strawberries and other fruits, sea shells and other designs. The objects and advantages of the ultra violet radiation shield are embodied in the following description.

DESCRIPTION OF DRAWINGS

FIG. 1 is a front elevational view of a female primate breast;

FIG. 2 is an enlarged sagittal sectional view taken along the line 2—2 of FIG. 1;

FIG. 3 is a front elevational view of the breast shield of the invention;

DETAILED DESCRIPTION OF PREFERRED EMBODIMENT

Figure 4:
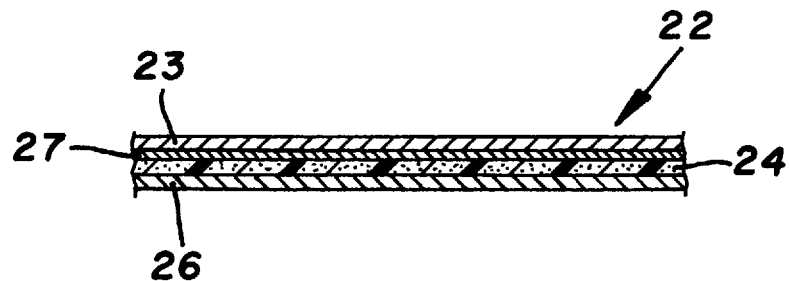
FIG. 4 is an enlarged sectional view taken along the line 4—4 of FIG. 3.

The ultra violet radiation shield of the invention, indicated generally at 22, inhibits exposure of body tissue of primates to short energy wave lengths in the ultra violet range. Shield 22 is usable by primates, including male and female humans, to protect selected parts of the body from solar and artificial ultra violet radiation. The following specification is directed to use of shield 22 by female humans to protect breasts from ultra violet radiation when exposed to solar radiation or artificial radiation in tanning booths. Shield 22 is also usable by male humans to protect selected areas of the anterior surface of the thorax and other body parts.

A female human breast 10 is shown in FIGS. 1 and 2. Breast 10 normally extends from the second through the sixth ribs 11, 12 from the sternum to the anterior line. Mammary tissue 13 lies directly over the pectoralis muscle 14. A layer of adipose tissue 16 is located between mammary tissue 13 and muscle 14. Mammary tissue 13 is surrounded by fatty tissue 15 covered with skin 21. The fully developed breast 10 has a generally dome shape with a central pigmented skin area 17, known as the areola mammae or areola. Skin area 17 normally has a diameter from 1½–2½ cm. The outer surface of area 17 has a rough appearance due to sebaceous glands 18 located directly beneath the skin. Glands 18 secrete a fatty substance which lubricates nipple 19. Bundles of smooth muscles in the areolar tissue serve to stiffen nipple 19.

Nipple 19 projects outwardly a few millimeters from areola 17 and has lactiferous ducts 21 surrounded by fibromuscular tissue and covered by skin. Ducts 21 extend inwardly toward muscle 14 and have enlarged areas or ampulla in which milk can be stored. Blood is supplied to breast 10 from the thoracic aorta, subclavian artery and the axillary artery. The ramifications of these arteries form a circular plexus around areola 17 which assured a blood supply to nipple 19 and areola 17. In addition to the vascular vessels, breast 10 has a network of lymph vessels which collect lymph from the central parts of gland, skin 21, areola 17 and nipple 19. The lymph vessels originate in the walls of the lactiferous ducts and collect lymph and carry lymph to other parts of the body, including the liver.

Skin 21, and its pigmentation and fatty tissue 15, below the skin, provide a limited natural shield from ultra violet radiation, indicated in FIG. 2 by arrows 22. Areola 17 and nipple 19, being muscular tissue, and blood and lymph vessels have a minimum ultra violet radiation shielding characteristics and allow ultra violet radiation into the mammary tissue 13, sebaceous glands 18 and blood vessels.

The ultra violet radiation, in addition to irritating and burning the skin of the areola 17 and nipple 19, has adverse effects on the tissues and blood vessels behind areola 17. Excess exposure of a person's bare body to ultra violet radiation, natural and artificial, will result in wrinkled skin, blisters, painful burns, and may result in melanoma. The ultra violet radiation also has adverse effects on the blood and lymph adjacent areola 17 and nipple 18, as well as the mammary tissue. These adverse effects include inducement of breast abscesses, Cooper's disease, tumors and cancerous tumors.

Figure 5:
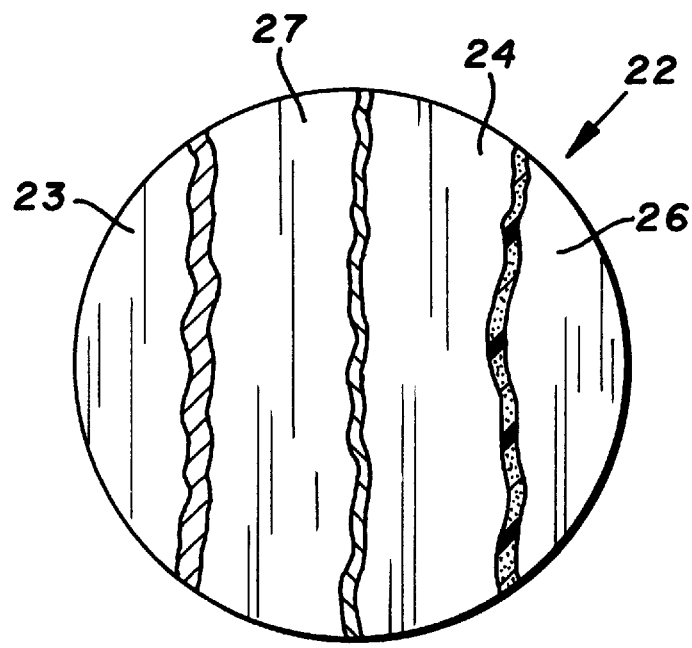
FIG. 5 is an enlarged front elevational view with layers sequentially broken away of the BREAST SHIELD.

Shield 10 is a multi-layered generally flat circular disc that can be attached to selected parts of the body, such as the areola 17 and nipple 18, as shown in FIG. 2. Referring to FIGS. 3, 4 and 5, shield 22 has a circular backing 23 comprising a rayon non-woven fabric with an acrylic binder. Other types of non-woven fabrics can be used for backing 23. Backing 23 is a circular disc member which has a diameter between 1½–2½ cm. Other sizes and shapes of backing 23 can be used. Located adjacent one side of backing 23 is an adhesive 24, such as a pressure sensitive acrylate, having hypo-allergenic properties, shown in FIGS. 3 and 4, at 24. A liner 26 covers the outer surface of adhesive 24. Liner 26 is a polyethylene-coated bleached craft paper. Liner 26 is removed from adhesive 24 before the shield is attached to the body tissue. Liner 26 protects the adhesive during transport and storage. Interposed between backing 23 and adhesive 24 is a layer of ultraviolet radiation reflective material, such as resin and metallic inks. An example of material 27 is a coating of aqua water-based screen ink having micro-metallic silver. One suitable ink is a 9500 Series Aqua Print RFU ink marketed by NAZDAR/KC, 1087 North Branch Street, Chicago, Ill. 60622. This ink is a water-dispersible lead heavy screen printing ink. Once printed, these inks must be heat-set for a period of time at 300 degrees F. Other types of materials that inhibit ultra violet radiation can be used with substrates including natural textiles, artificial textiles, vinyls and other plastics. Material 17 is an ultra violet radiation blocking layer or film that shields the person's body part, such as areola 17 and nipple 19, from solar and artificial ultra violet radiation. The ultra violet radiation material can be incorporated into the adhesive.

The outer surface of backing 23 can have varying shades of colors and can include artistic, ornamental and graphic designs, such as flowers, beach balls, chocolate chips, strawberries, sea-shells and other ornamental designs that enhance the ornamental design of the shield.

In use, liner 26 is peeled from adhesive 24. The shield is then placed over the selected body part, such as the areola 17 and nipple 19, as seen in FIG. 2. Shield 22 protects the selected body part from the ultra violet radiation, as indicated by the broken arrows 28 in FIG. 2. Shield 22 inhibits ultra violet radiation from effecting the blood, lymph and mammary tissues 13, as well as the skin of the areola 17 and nipple 19. Shield 22 may be readily removed from breast 10, as the adhesive 24 is a pressure sensitive material which does not irritate the skin. Shield 22 is quickly pulled from the skin. One or more shields 22 are used to protect the areola and nipples of the breast for sunbathers and tanners of all ages, including male and female humans that desire uniform tanning without strap or clothing marks.

Figure 6:
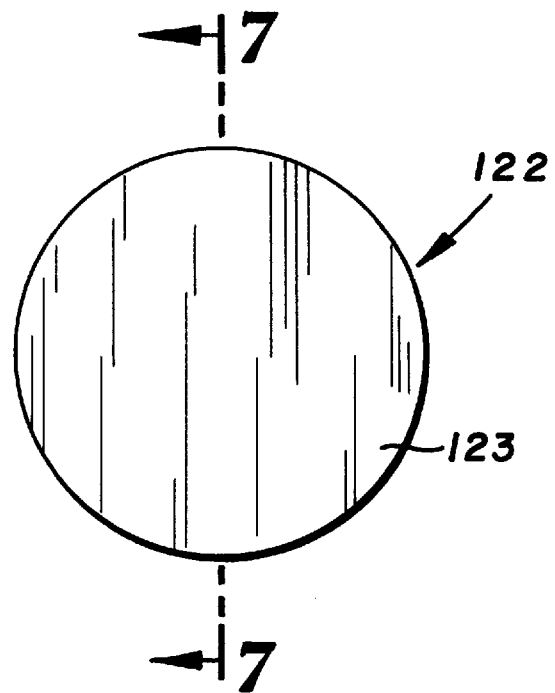
FIG. 6 is a front elevational view of a modification of the ultra violet radiation shield of the invention.
Figure 7:
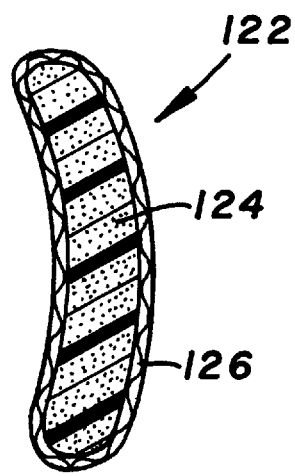
FIG. 7 is an enlarged sectional view taken along the line 7—7 of FIG. 6.

Referring to FIGS. 6 and 7, there is shown a modification of the ultra violet radiation shield of the invention, indicated generally at 122. Shield 22 is shown as a circular disc or pad 123 that is adapted to be used with fabrics and clothing to position the shield adjacent a selected body location. As shown in FIG. 7, shield 122 has a generally convex-shaped core or substrate 124 of foam plastic material, such as polyurethane. The ultra violet radiation blocking material is incorporated into the core 124. A cover 126 surrounds core 124. The cover can be a fabric, such as cotton, nylon, rayon and the like. The shield can be used without cover 126.

Figure 8:
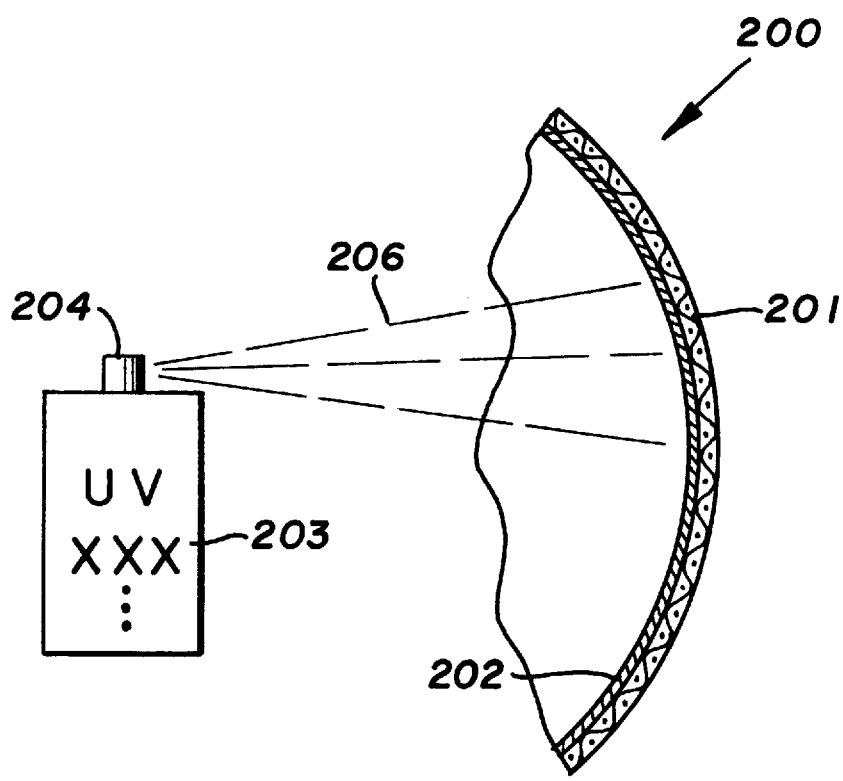
FIG. 8 is a diagrammatic view showing spraying of ultra violet radiation material on a garment.

Referring to FIG. 8, there is shown a further modification of an ultra violet radiation shield incorporated into an article of clothing, indicated generally at 200. Article 200 is illustrated as a portion of a female bra or a male bro. The article has a fabric 201 base with an inside surface that is covered with a coating or layer 202 of ultra violet radiation blocking material. Material 202 is applied to fabric 201 with a spray container 203 having a discharge nozzle 204 that is actuated to direct spray 206 of material onto the inside surface of fabric 201. Spray 206 can be water-based ink, as disclosed as an example of the material 27 described herein. Other types of materials that inhibit ultra violet radiation can be applied to fabric 201.

While there has been shown and described an embodiment of the ultra violet radiation shield for a primate's breast, it is understood that the shield can have other sizes and shapes for protecting various parts of a primate's body. The shield can be made of various structures, adhesives and ultra violet radiation blocking substances that are within the scope of the invention. The invention is defined in the following claims.

I claim:

1. An ultra violet radiation shield for protecting a person's skin from ultra violet radiation comprising: a backing member having first and second sides, adhesive means located adjacent one side of the backing member for holding the shield on a person's skin, liner means covering the adhesive means to protect the adhesive means, said liner means being removable from the adhesive means whereby the adhesive means can be placed on a person's skin, and ultra violet radiation blocking means comprising an ink having ultra violet radiation blocking properties located between the first side of the backing member and the adhesive means for protecting the person's skin from ultra violet radiation, said adhesive means secured to and covering the ultra violet radiation blocking means, said backing member, adhesive means and ultra violet radiation blocking means being secured together to form said ultra violet radiation shield.

2. The ultra violet radiation shield of claim 1 wherein: the backing member is a rayon non-woven fabric having an acrylic binder.

3. The ultra violet radiation shield of claim 1 wherein: the backing member is a circular disc.

4. The ultra violet radiation shield of claim 1 wherein: the adhesive means is a pressure sensitive acrylate having hypo-allergenic properties.

5. The ultra violet radiation shield of claim 1 wherein: the liner means is a craft paper.

6. An ultra violet radiation shield for protecting the areola and nipple of a primate's breast from ultra violet radiation comprising: a backing member having first and second sides of a size to cover the areola and nipple of a primate's breast, ultra violet radiation blocking means comprising an ink having ultra violet radiation blocking properties covering the first side of the backing member for protecting the areola and nipple from ultra violet radiation, adhesive means attachable to at least the areola of the breast, said adhesive means secured to and covering the ultra violet radiation blocking means whereby the ultra violet radiation blocking means is located between the backing member and the adhesive means, and liner means covering the adhesive means to protect the adhesive means, said liner means being removable from the adhesive means whereby the adhesive means can be attached to the areola.

7. The ultra violet radiation shield of claim 6 wherein: the backing member is a circular, flexible rayon non-woven fabric having an acrylic binder.

8. The ultra violet radiation shield of claim 6 wherein: the adhesive means is a pressure-sensitive acrylate having hypo-allergenic properties.

9. The ultra violet radiation shield of claim 6 wherein: the liner means is a craft paper.

10. An ultra violet radiation shield for protecting a person's skin from ultra violet radiation comprising: a backing member having a first side and a second side, and ultra violet radiation blocking means comprising an ink having ultra violet radiation blocking properties secured to and covering the first side of the backing member for protecting the person's skin from ultra violet radiation.

11. The ultra violet radiation shield of claim 10 wherein: the backing member is a rayon-woven fabric having an acrylic binder.

* * * * *